United States Patent [19]

Proudian

[11] 4,194,510
[45] Mar. 25, 1980

[54] ULTRASONIC FOCUSING SYSTEM

[75] Inventor: Andrew P. Proudian, Chatsworth, Calif.

[73] Assignee: Second Foundation, Inc., Woodland Hills, Calif.

[21] Appl. No.: 915,783

[22] Filed: Jun. 15, 1978

[51] Int. Cl.$^2$ .............................................. A61B 10/00
[52] U.S. Cl. ..................................... 128/660; 73/629
[58] Field of Search ................. 128/660, 661; 73/629, 73/628, 625, 606; 340/5 H, 5 MP

[56] References Cited

U.S. PATENT DOCUMENTS

| | | | |
|---|---|---|---|
| 3,969,578 | 7/1976 | Mezrich et al. | 73/606 |
| 4,084,582 | 4/1978 | Nigam | 128/660 |

*Primary Examiner*—Willis Little

[57] ABSTRACT

A system for dynamically focusing ultrasonic waves consisting of a housing filled with a liquid media, an ultrasonic transducer, a reflector, and a control device. The ultrasonic transducer, located within the housing, emits ultrasonic waves and detects echoes of the ultrasonic waves as they return from the object being scanned. The reflector is also located within the housing and is positioned so as to intercept and redirect the ultrasonic waves and the resulting echoes. The reflector consists of a flexible reflective membrane which is stretched across an air filled enclosure. The control device is located adjacent the housing and consists of a member adapted to variably compress the liquid media contained in the housing so as to provide pressure variations to the reflective membrane. These pressure variations periodically deform the reflective membrane so that the ultrasonic waves from the transducer are reflected to converge at a point a preselected distance beyond the reflector and the echoes returning from a preselected range within the scanned object are in focus approximately at the ultrasonic transducer surface.

25 Claims, 3 Drawing Figures

ULTRASONIC FOCUSING SYSTEM

BACKGROUND OF THE INVENTION

1. Field of the Invention

The present invention relates to the field of ultrasonic scanners, and in paticular to pulse echo ultrasonic or sector scanners for use in medical diagnostics.

2. Prior Art

Ultrasonic scanning instruments are used in medical diagnostics to view regions or particular organs within the body without the necessity of surgical incission to expose the area of interest. In its most fundamental operation, the ultrasonic scanning instrument is placed in contact with surface of the body to be examined. The scanning instrument then emits a series of pulses, at an ultrasonic frequency, into the body being examined. During the time between the emissions of the pulses, the instrument searches for and detects echoes of the emitted pulses which have been reflected by the various internal objects of interest. It is these echoes and their relationship to the emitted pulses, which generates a representation or a "view" of the internal region or organs of interest.

In present day ultrasonic scanning instruments, focused ultrasound transducers are used in order to improve the resolution of the scanning instrument. Most such focused devices achieve focusing by means of a curved transducer element or by use of an acoustic lens generally attached to the front face of a planar transducer element. Of particular importance in such devices is the focal zone or linear distance in which the device is in focus. Typically, the focal zone, having a length L, of such focused devices is small, being approximately equal to $L = f^2/A2\lambda$, where f is the focal length, $\Lambda$ is the transducer or lens effective aperture diameter and $\lambda$ is the wavelength of the ultrasonic wave generated by the transducer. For a typical transducer operating frequency of 2.25 MHz, $\lambda = 0.068$ cm, and for a typical focal length $f = 10$ cm and $\Lambda = 1.3$ cm, the focal zone is only about 4 cm in length, whereas the extent of the zone of interest is typically 10 to 15 cm in most applications of diagnostic ultrasound.

A variety of methods may be used in an attempt to increase the focal zone of an ultrasonic scanning instrument. For example, the length of the focal zone can be increased by reduction of the transducer diameter, but this would degrade resolution and sensitivity and defeat the purpose of focusing. Also, a soft-focusing technique may be used whereby the focal zone is stretched by appropriate lens design at the expense of degraded resolution throughout the longer focal zone. Such a soft-focusing technique is disclosed in "Design of Narrow-beamwidth Transducers" by G. Kossoff in volume 35 of the Journal of the Acoustical Society of America (1963) at page 905. However, this technique represents a less than satisfactory compromise. Another possibility is to use a water bath of variable length to couple the transducer output to the patient, and then move the focal zone within the body to be examined by moving the transducer within the water path. Such a technique was disclosed by W. J. Fry, et al., in their article "Ultrasonic Visualization System Employing New Scanning and Presentation Methods" in volume 44 of the Journal of the Acoustical Society of America (1968) at page 1324. This is a relatively slow and cumbersome procedure, however, and cannot be used when rapid scanning is required, as in echocardiography or fetal scanning.

A technique which provides focusing throughout a relatively long focal zone without resolution degradation and which has recently been applied to diagnostic ultrasound devices is so called electronic focusing. This technique provides an electronically variable focus by use of an array transducer, the focus being cylindrical if a linear array is used, or spherical if an annular array is used. Such systems are described by H. E. Melton, Jr., in "Electronic Focal Scanning for Improved Resolution in Ultrasound Imaging," a Doctorate Thesis, Duke University, Durham, N. C. 1971 and by Von Ramm et al., in "Improved Resolution in Ultrasound Tomography," published in the Proceedings of the 25th Annual Conference on Engineering in Medicine and Biology (1972) at page 141.

The main drawback in electronically focused phased array systems lies in their complexity and cost. In order to provide good focusing and beam forming properties, the array systems must be made up of a relatively large number of elements. Ideally, in a uniform array, elements which are one half wavelength or less in width would be used. Since array diameters must be typically fifteen to twenty-five wavelengths in order to provide good resolution, the minimum beam width achievable being approximately $f = \lambda/\Lambda$, an array with near ideal beam characteristics should contain thirty to fifty elements. On the other hand, non-uniform arrays with fewer elements are possible at the expense of more complex delay electronics. The phased array including its delay line, switching, circuitry and amplification electronics for either array system is at present quite complex and expensive. Furthermore, in certain mechanically scanned systems, such as the ones described in a copending application by Proudian et al., Ser. No. 876,989, filed Feb. 13, 1978, it is not possible to use electronic focusing since the beam forming in these devices is achieved by rotating (acoustical) optics, not by a transducer which emits a plane wave.

Accordingly, it is a general object of the present invention to provide an improved ultrasonic focusing means.

It is a further object of the present invention to provide a simple and relatively inexpensive means to achieve dynamic focusing of an untrasound beam.

It is yet another object of the present invention to provide a means for dynamic focusing of an acoustic beam which does not require the use of a transducer array or phased array electronics.

It is still another object of the present invention to provide a means of moving the focal zone of an ultrasound diagnostic instrument within a body being examined without mechanical displacements of the transducer.

It is yet another object of the present invention to provide a means of providing variable focusing for mechanical scanners which utilize rotating transducer optics.

SUMMARY OF THE INVENTION

An ultrasonic beam focusing system is provided. The system includes a housing which is substantially filled with a liquid media, an ultrasonic transducer, a reflector means, and a control means. The ultrasonic transducer is disposed within the housing and is adapted to emit ultrasonic waves and detect echoes of those ultrasonic waves. The reflector means is disposed within the housing so as to intercept and redirect the ultrasonic waves and echoes. The reflector means is comprised of a flexible reflective membrane which is stretched across an enclosure filled with a media which is substantially more compressible than the liquid media contained in the housing. The control means is disposed adjacent the housing and is comprised of a member which is adapted to variably compress the liquid media contained in the housing. This variable compression of the liquid media couples pressure variations to the reflective membrane, so as to periodically deform the reflective membrane such that the ultrasonic waves are reflected to converge at a point a preselected distance beyond the reflector means. The reflective membrane is then variably deformed so as to cause echoes emanating from a range of distances beyond the reflector means to be in focus, that is, at the transducer, the wavefronts of the returing echoes are caused to assume the shape of the wavefronts of waves leaving the transducer.

The novel features which are believed to be characteristic of the invention, both as to its organization and its method of operation, together with further objects and advantages thereof, will be better understood from the following description in connection with accompanying drawings in which a presently prefered embodiment for the invention is illustrated by way of example. It is to be expressly understood, however, that the drawings are for purposes of illustration and description only and are not intended as a definition of the limits of the invention.

DETAILED DESCRIPTION OF THE INVENTION

Figure 1:
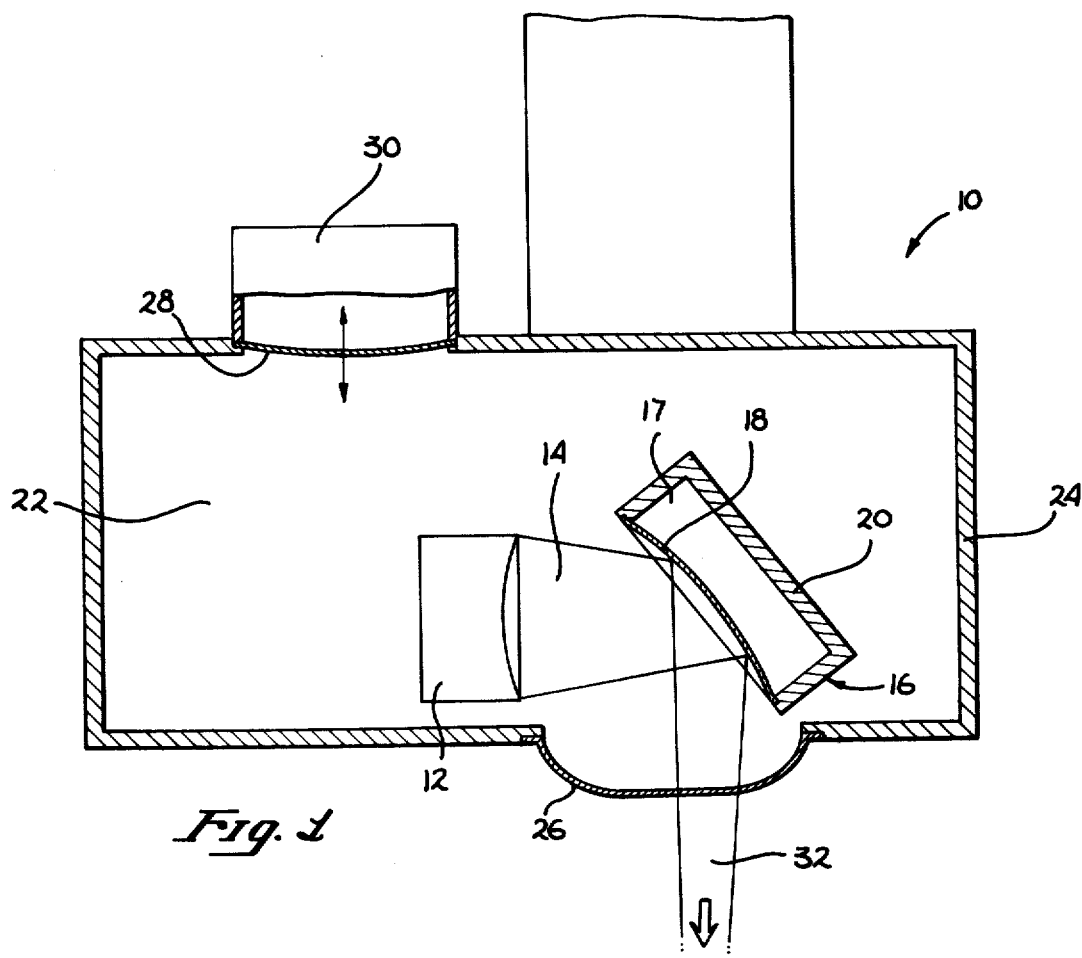
FIG. 1 is a schematic diagram of the focusing system of the present invention.

Referring now to FIG. 1, a scanning head 10 incorporating a preferred embodiment of the present invention is illustrated. An ultrasonic transducer 12 is shown generating a beam 14 of untrasonic signals which is incident on the variable focusing reflector means 16. Variable focusing reflector means 16 is comprised of a circular flexible membrane 18 which is rigidly attached along its outer edge to a cylindrical enclosure 20, thus effectively forming a drum. A liquid coupling media 22 fills the scanning head 10 and is contained by the scanning head walls 24, the sonolucent dome 26 through which the ultasonic beam 32 exits, and the pressure control plate 28.

Pressure control plate 28 may be a deformable plate or membrane rigidly attached to the walls 24 of the scanner 10, or a rigid plate attached to walls 24 by metal bellows. The pressure control plate 28 acts as a piston, and as is described more fully hereinbelow, controls the shape of the reflecting surface of flexible membrane 18. Motion of the plate 28 is achieved by a driver means 30.

Cylindrical enclosure 20 is filled with a gaseous media 17 whose compressibility is substantially greater than the compressibility of liquid media 22. In the presently preferred embodiment, the gaseous media 17 in the cylindrical enclosure 20 is air, although a variety of other gases may be effectively used. Because of the very large difference in acoustic impedance between the liquid media 22 on one side of the membrane 18 and air 17 on the other side, the membrane 18 acts as a perfect reflector for the ultrasound energy impinging upon it. The membrane 18 material and thickness can therefore be selected to provide the optimum weight and flexural or tensile strength characteristics without regard to its acoustic reflection properties, so long as its thickness is very small compared with the wavelength of the signals of beam 14.

The principle of operation of the focusing system of the present invention is based in part on the much greater compressibility of air 17 compared to that of the liquid coupling media 22. As a consequence, the media 22 acts essentially as an incompressible medium, transmitting increases or decreases in pressure exerted by the control plate 28 to the membrane 18, the membrane 18 being thereby deformed. That is, since the volume of the media 22 in the scanner head 10 remains approximately constant, displacements or deformations of the control plate 28 are compensated for by corresponding deformations of the membrane 18. In the presently preferred embodiment, liquid coupling media 22 is water or glycerol, although a variety of other liquids may be effectively used.

Movement or deformation of the plate 28 can be achieved by a variety of means. In the presently preferred embodiment, the driver means 30 is a voice coil and magnet arrangement, similar to that used in dynamic loudspeakers. Such voice coil and magnet arrangements are disclosed in Acoustics, 2nd ed. (1964), published by Wiley, New York, which is incorporated herein by this reference. Of course, other driver means may be used, including the mechanisms of direct radiator speaker arrangements, where the voice coil would be attached to the back of plate 28. Also, the pressure control element need not be a plate, but could be an inflatable balloon or other means of transmitting pressure variations to the membrane 18. In an alternate embodiment, membrane 18 is deformed by electrostatic or electromagnetic means which are directly coupled to membrane 18.

However, the use of pressure plat 18 or other means of coupling pressure variations to reflector means 16 offers a distinct advantage over other methods of deforming member 18 since a single plate or piston, with fixed electrical contacts, can control the deformation of a large number of reflector means 16. Thus, one pressure plate may be used to control the focal length for many reflectors in a mechanical sector scanner which utilizes rotating transducer optics, such as the one disclosed in the copending application of Proudian, et al., Ser. No. 876,989, filed Feb. 13, 1978.

Figure 2:
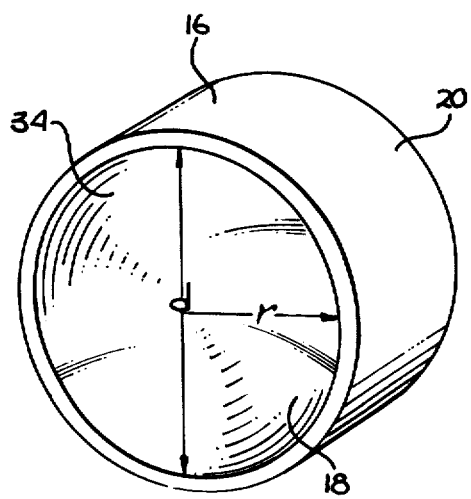
FIG. 2 is a perspective view of the variable focusing reflector means of the present invention.

Now referring to FIG. 2, the variable focusing reflector means 16 is shown in greater detail. Reflector means 16 is comprised of a flexible membrane 18 which is stretched across a cylindrical enclosure 20. Flexible membrane 18, which in FIG. 2 is shown having a concave configuration, has a diameter d and a radius r. As described hereinabove, flexible membrane 18 acts as a reflecting surface for acoustic waves due to the variation in acoustic impedance the liquid media 22 and the gaseous media 17 contained within cylindrical enclosure 20.

The shape of the reflector membrane 18 will be determined by the pressure forces transmitted to it by the liquid coupling media 22, the pressure forces applied by the air 17 in the cylindrical enclosure 20, and by the elastic properties of the membrane 18. Static deformation of the membrane 18, and therefore static adjustable focusing is easily achieved merely by displacement of the pressure control plate 28 due to the passing of a constant current through the voice coil of driver means 30. The membrane 18 will achieve an approximately spherical curvature, with a radius of curvature determined by the area and displacement of plate 28, and a focal length f equal to half that radius of curvature. However, dynamic focusing is more difficult to achieve than static focusing.

The basic problem in achieving dynamic focusing by means of deformable optics is that the transducer in most ultrasound pulse echo diagnostic scanners acts as both a transmitter and receiver. When the acoustic pulse is transmitted by the transducer, the receive focus or the focal zone of the transducer must track the echoes from the transmitted pulse throughout a range of interest, that is, from a minimum distance $R_{min}$ to the maximum distance $R_{max}$. This tracking of echoes throughout a range of interest requires that the echoes be in focus regardless of their point of emanation, that is at the transducer, the wavefronts of the echoes must be caused to assume the shape of the wavefronts of waves leaving the transducer.

The range $R(t)$ of the echoes, measured from the reflecting membrane 18, may be written as a function of time: $R(t) = C/2t$, where t is the time the transmitted pulse takes to go from the reflecting mirror 18 to the point of interest, a distance R, and where c is the mean speed of sound in the liquid coupling media 22. The system focus location, if it is to track the returning echo throughout the range of interest, must therefore shift from a transmit focus range $R_o$ to the minimum range of interest $R_{min}$, in the time interval $t_1 = 2/c\ R_{min}$, then track the echo between $R_{min}$ and $R_{max}$, then shift to the transmit range again in the time interval $t_2 = (T - 2/c\ R_{max})$. The time interval $T' = 2/c\ (R_{max} - R_{min})$ is the useful portion of the pulse interval T guring which time the echo may be tracked. On the other hand, the time $\tau = t_1 + t_2$ is the 'dead time' during which time the focus is shifting to or from the echo tracking focus. The useful portion T' of the pulse period T plus the dead time is the total pulse period T. Since a high duty cycle is sought in most scanning applications, it is necessary to select operating parameters such that $\tau << T$. Typically, $R_{min} = 5$ cm, when measured from the membrane 18, $T = 333 \mu$sec for a 3000 Hz pulse frequency, $R_{max} = 23$ cm, so that $t_1 = 67\ \mu$ sec, $t_2 = 25\ \mu$ sec, $\tau = 92\ \mu$ sec.

Figure 3:
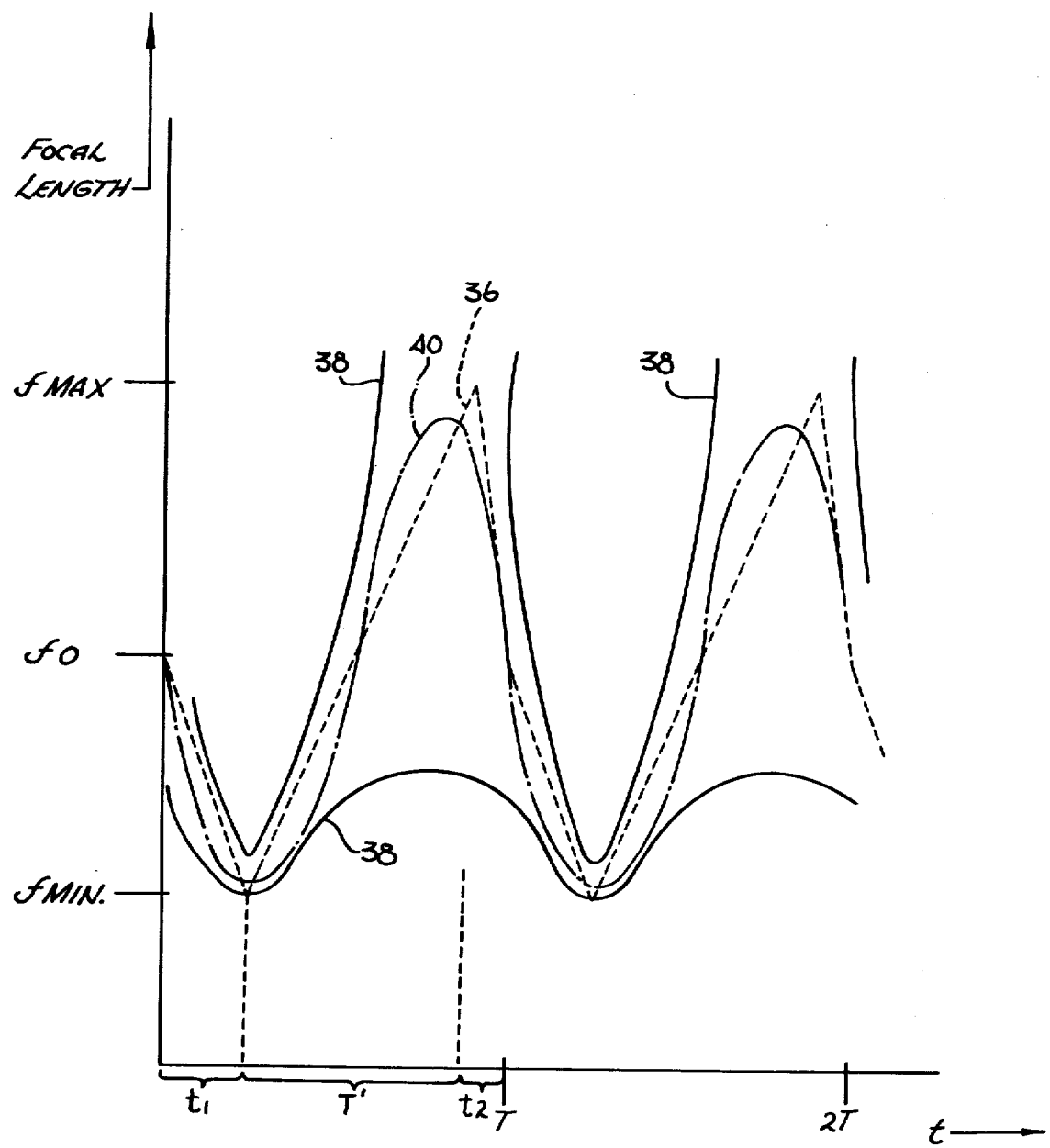
FIG. 3 is a graph of the focal length of a transducer versus time which illustrates the variation in focal length of the reflector means of the present invention.

From the above discussion, it can be seen that while the motion required of the focus in dynamic focusing is periodic, with period T, it is not a simple periodic motion, but rather consists of a relatively slow linear motion between $t_{min} = 2/c\ R_{min}$ and $t_{max} = 2/c\ R_{max}$, and two rapid (but otherwise arbitrary) motions in the time intervals $t_1$ and $t_2$. A graph of this motion is illustrated as plot 36 in FIG. 3. From FIG. 3 it can be seen that the focus of scanner head 10 starts at a transmit focus $f_o$ at which time the transducer 12 emits a very short interrogating pulse. Then, the focus must shift from the transmit focus $f_o$ to the minimum echo receive focus point $f_{min}$ in a time $t_1$. Then the focus changes linearly from $f_{min}$ to $f_{max}$, during which time scanner head 10 is searching for echoes from the interrogating pulse in the range of interest in a time T'. Finally, the focus must rapidly shift back to the transmit focus $f_o$ in a time $t_2$ so that the whole process may be repeated. In the extreme case where no dead time is allowed, the required motion of the focus would be a sawtooth motion, but this clearly cannot be achieved by physically realizable mechanical deformations. Even for the typical example described by plot 36 in FIG. 3, exact tracking of the echo between $R_{min}$ and $R_{max}$ is extremely difficult to achieve by mechanical means since it requires a frequency response of the membrane 18 of many tens of thousands of cycles per second.

It can be shown by mechanics and optics considerations that the focus of scanner head 10 will be located a distance f in front of the membrane 18 where f is given approximately by the formula:

$$f = f_o (1 + \frac{1}{1 + \frac{16 f_o z}{d^2}})$$

where $f_o$ is the focal distance for the beam 14 impinging on membrane 18 when member 18 is flat, d is the diameter of the membrane 18 and z is the distortion parameter, i.e., the displacement of the membrane center from its equilibrium position. From this equation, the frequency characteristics of the distortion parameter z can be determined from the required behavior of f, previously discussed. It is important to note that this equation is valid only if the deformation of the membrane 18 is monotonic, as a function of radial position r on the membrane 18, going from its maximum z at the center ($r = 0$) to zero at the edges ($r = d/2$), without any nodes in between. This monotonic deformation is a most important consideration, since only the portion of the membrane 18 up to the first node is useable to reflect and refocus the ultrasound beam 14. Thus it can be seen that only frequencies of motion below the fundamental resonance frequency $\nu_R$ of the reflector means 16 are useful in synthesizing the motion $z(t)$.

The maximum resonant frequency $\nu_R$ is limited by two factors, the first being the physical limitations of achieving high resonant frequencies for a drum of diameter d typically equal to 1 to 2 cm. The need for high resonant frequencies is one of the reasons for selection of the air backed reflector membrane 18 to act as a deformable optical element, since a very thin and light membrane 18 can be used, and the 'spring constant' can be provided by the air in the drum. Typically, a 1.5 cm diameter 50 microns thick polyester membrane stretched over a 0.15 cm deep drum will provide a fundamental resonance at about 15 KHz.

The other limitation on the highest useable frequency component $V_R$ in membrane 18 deformation relates to the use of the pressure control plate 28 to generate the pressure field which drives the deformation of the membrane 18. In order to avoid radiating large amounts of acoustic power into the liquid 22, it is necessary to insure that the corresponding acoustic wavelength $\lambda_R = c/\nu_R$ of the pressure field be significantly larger than the circumference $L_p$ of the plate 28 as well as the mean distance D from the plate 28 to the membrane 18. Since typically D approximately equals $L_p$ which approximately equals 6 cm, and $c = 1.6 \times 10^5$ cm/sec, then if it is required that $\lambda_R \geq 2.5D$, it is found that $\nu_R$ must be less than 13.5 KHz. Thus, the maximum frequency of the function $z(t)$ is limited to 10 KHz to 15 KHz.

Of course, since $z(t)$ is periodic with period T, $z(t)$ must be synthesized with harmonics of the pulse repetition frequency $\nu_p = 1/T$. For the typical case where $\nu_p = 3000$ Hz, the available frequencies below 13.5 Khz are then the fundamental, $\nu_p = 3$ KHz and the first three harmonics at 6 KHz, 9 KHz and 12 KHz. The motion f(t) will contain additional harmonics since f(t) is a non-linear function of z, although it does not deviate greatly from linearity because the quantity $16f_oz/d^2$ will be small compared to unity nearly throughout the range of z, in practical applications. With the above limitations on synthesizing z(t), it is not possible to track the receive echo exactly and place the transmit focus at the desired range, for practical cases where $\nu_p$ is typically several thousand Hertz, without severe limitations on the tracked range interval $R_{max} - R_{min}$ and excessively long dead time.

In the present invention, therefore, no attempt is made to have the nominal focus track the return echo in range exactly. In fact, it is not necessary to have exact tracking to achieve the objective of dynamic focusing, i.e. to provide a resolution equal to that at the focus over the range interval of interest. Instead, it is only necessary that the received echo range at any time lie within the focal zone of the receiver, which is not a point, but rather an interval of length $L = f^2/\Lambda^2 \lambda$, where $\Lambda$ is the effective aperture diameter and $\lambda$ the wavelength centered about the nominal focus. A representative graph of the focal zone is illustrated as the area between the lines 38 in FIG. 3.

In the focal zone of length L, the beam width remains approximately constant, so that the resolution is at or near the diffraction limited value $f\lambda/\Lambda$. Thus, in the present invention, the deformation z(t) is controlled so as to maintain the condition:

$$|f(t) - R(t)| \leq \frac{1}{2} \frac{f^2}{\Lambda^2} (t)\lambda$$

This proximate, rather than exact, tracking is easily achieved with a motion of z(t) having a frequency spectrum comprised of three or four frequency components, i.e., frequency components including the fundamental $\nu_p$ and the first two or three harmonics. In fact, good focusing range can be achieved just with a sinusoidal motion at frequency $\nu_p$. Such a sinusoidal motion is shown as plot 40 in FIG. 3. As described hereinabove, the motion desired of z(t) is produced by supplying an alternating current to the voice coil of driver means 30. Thus, this alternating current would have a frequency spectrum similar to that of z(t), i.e., either a single sinusoid or a plurality of frequency components.

It is important to note that the value of $\frac{1}{2} L(t)$, which is the tracking tolerance, is proportional to $f^2(t)$, so that it becomes increasingly more difficult to maintain the dynamic focusing at very short ranges. However, since the present invention is intended for use with water path type scanners, and the focal length f(t) is measured from the face of the membrane 18, which is typically several centimeters within the scanner 10, it is normally not necessary to focus much closer than approximately 5 cm.

Focusing all the way out to the maximum range is also generally not possible because the time $t_2$ avaliable to switch from $R_{max}$ to the transmit range $R_o$ is very short without encountering significantly increased dead time. Thus, for example, in the typical case discussed previously in which $R_{min} = 5$ cm and $R_{max} = 23$ cm (corresponding to a range of interest within the body of 2 to 20 cm, for a typical water path length of 3 cm), and T = 333 $\mu$sec, the last one centimeter of the echo range will lie outside the focal zone. Note however that the echo will still be far better focused, i.e., have much better resolution, than with a fixed system typically focused at say $R_o = 13$ cm (i.e. 10 cm in the body).

Also, when the echo range lies outside the focal zone for the near ranges, for example, R less than 5 cm, the resolution in the near range is also better than for a fixed focus system, since the focal length 'error' will be considerably less than a fixed focal length system. The above considerations apply equally whether the beam 14 incident on the membrane 18 is unfocused, strongly focused, or weakly focused.

In the presently preferred embodiment, an unloaded uniform thickness membrane is used as the membrane 18. It is possible, however, to utilize non-uniform membranes which will result in deformations that are other than the Bessell function shape assumed by such a uniform membrane, in order to provide more subtle beam shaping effects.

One further advantage of the present invention is that the power required to achieve a displacement of the membrane 18 center of a few tens of microns is quite minimal, because in effect, it is the air 17 in the enclosure 20 which is being compressed rather than the liquid media 22. Acoustic radiation losses into the liquid 22 are minimized both because of the 'slack' provided by the proximity of the enclosure 20 and by the fact that the wavelength of sound in the liquid media 22 is much greater than the diameter d' of the pressure control plate 28, which typically will be comparable to the membrane 18 diameter d. Note that when d' is approximately equal to d, the displacement amplitude a' of the pressure control plate 28 will also be approximately equal to the displacement amplitude of the center of membrane 18. Most of the mechanical power dissipation in the system will come from the friction associated with the deformation of the plate 28 or of the deformable structure (e.g., metal bellows) by which the plate 28 is attached to the scanner wall 24, and is of the order of a tenth of a watt.

Thus, it can be seen from the above description that the present invention provides a simple and relatively inexpensive means for providing dynamic focusing of an ultrasonic beam. The dynamic focusing provided by the present invention greatly improves the resolution of an ultrasonic scanning instrument throughout the range of interest without the cost and complexity of a transducer array or phased array electronics, and without the inconvenience of moving the transducer relative to the object being examined. Yet, this improvement in resolution is brought about by the use of simple devices, primarily by the use of a reflective "drum" and virtually any means for providing a deformation of the reflective surface of that drum.

While a specific embodiment of the present invention has been disclosed and described in detail herein, it will be understood by those skilled in the art that various changes in form and detail may be made therein without departing from the spirit and scope of the invention.

I claim:
1. An ultrasonic focusing system comprising:
   a housing substantially filled with a liquid media;
   an ultrasonic transducer disposed within said housing for emitting ultrasonic waves and detecting echoes of said ultrasonic waves;
   reflector means disposed within said housing so as to intercept and redirect said ultrasonic waves and said echoes, said reflector means comprised of a flexible acoustically reflective membrane; and control means disposed within said housing and coupled to said reflector means via said liquid media, whereby said control means periodically deforms said reflective membrane such that said ultrasonic waves are reflected to converge at a point a preselected distance beyond said reflector means, and such that said echoes are reflected so as to be substantially in focus at said ultrasonic transducer substantially throughout the range of distances of interest over which the echoes are detected.

2. The system of claim 1 wherein said control means is comprised of a member adapted to couple variations in pressure to said reflective membrane.

3. The system of claim 2 wherein said reflective membrane is stretched across an enclosure filled with a media which is substantially more compressible than said liquid media, and said control means is comprised of a member adapted to variably compress said liquid media so as to couple pressure variations to, and thereby selectively deform, said reflective membrane.

4. The system of claim 3 wherein said member is a pressure plate adapted to move in and out of said housing so as to exert a variation in pressure on said liquid media.

5. The system of claim 4 wherein said control means is further comprised of electromagnetic means coupled to said pressure plate and adapted to move said plate in and out of said housing.

6. The system of claim 4 wherein said control means is further comprised of electrostatic means coupled to said pressure plate and adapted to move said pressure plate in and out of said housing.

7. The system of claim 3 wherein said member is a membrane adapted to selectively deform into said housing so as to exert a variation in pressure on said liquid media.

8. The system of claim 1 wherein said control means is comprised of electromagnetic means adapted to periodically deform said reflective membrane.

9. The system of claim 8 wherein said reflective membrane is stretched across an enclosure filled with a media which is substantially more compressible than said liquid media, and said control means is further comprised of a member coupled to said electromagnetic means and adapted to variably compress said liquid media so as to couple pressure variations to, and thereby selectively deform, said reflective membrane.

10. The system of claim 1 wherein said control means is comprised of electrostatic means adapted to periodically deform said reflective membrane.

11. The system of claim 10 wherein said reflective membrane is stretched across an enclosure filled with a media which is substantially more compressible than said liquid media, and said control means is further comprised of a member coupled to said electrostatic means and adapted to variably compress said liquid media so as to couple pressure variations to, and thereby selectively deform, said reflective membrane.

12. An ultrasonic focusing system comprising:
a housing substantially filled with a liquid media;
an ultrasonic transducer disposed within said housing for emitting ultrasonic waves and detecting echoes of said ultrasonic waves;
reflector means disposed within said housing so as to intercept and redirect said ultrasonic waves and said echoes, said reflector means comprised of a flexible acoustically reflective membrane which is stretched across an enclosure filled with a media which is substantially more compressible than said liquid media; and
control means disposed adjacent said housing and comprised of a member adapted to variably compress said liquid media so as to couple pressure variations to said reflective membrane, whereby said pressure variations periodically deform said reflective membrane such that said ultrasonic waves are reflected to converge at a point a preselected distance beyond said reflector means, and such that echoes are reflected so as to be substantially in focus at said ultrasonic transducer substantially throughout the range of distances of interest over which echoes are detected.

13. The system of claim 12 wherein said control means is further comprised of a driver means coupled to said member and adapted to move said member in and out of said housing so as to variably compress said liquid media.

14. The system of claim 13 wherein said driver means moves said member such that said reflective membrane is first deformed so as to reflect said ultrasonic waves at a point a preselected distance beyond said reflector means and then is variably deformed so as to converge echoes eminating from a range of distances beyond said reflector means substantially at said ultrasonic transducer.

15. The system of claim 14 wherein said driver means moves said member such that said reflective membrane is caused to deform in an oscillatory manner at one preselected frequency.

16. The system of claim 15 wherein said media contained in said enclosure of said reflector means is air.

17. The system of claim 14 wherein said driver means moves said member such that said reflective membrane is caused to deform in an oscillatory manner with a frequency spectrum having a plurality of frequency components.

18. The system of claim 17 wherein said media contained in said enclosure of said reflector means is air.

19. The system of claim 13 wherein said driver means is comprised of a voice coil and magnet, said voice coil having electrical couplings for supplying current thereto.

20. The system of claim 19 wherein an alternating current at one preselected frequency is supplied to said voice coil.

21. The system of claim 20 wherein said media contained in said enclosure of said reflector means is air.

22. The system of claim 19 wherein an alternating current having a frequency spectrum comprised of a plurality of frequency components is supplied to said voice coil.

23. The system of claim 22 wherein said media contained in said enclosure of said reflector means is air.

24. An ultrasonic focusing system comprising:
a housing substantially filled with a liquid media;
a plurality of ultrasonic transducers disposed within said housing, each said transducer adapted to emit ultrasonic waves and detect echoes of said ultrasonic waves;
a plurality of reflector means disposed within said housing, each said reflector means adapted to intercept and redirect said ultrasonic waves and said echoes, each said reflector means comprised of a flexible acoustically reflective membrane which is stretched across an enclosure filled with a media which is substantially more compressible than said liquid media; and control means disposed adjacent said housing and comprised of a member adapted to variably compress said liquid media so as to couple pressure variations to each said reflective membrane, whereby said pressure variations periodically deform said reflective membranes such that said ultrasonic waves are reflected to converge substantially at a point a preselected distance beyond said reflector means, and such that echoes are reflected so as to be substantially in focus at said ultrasonic transducers.

25. The system of claim 24 wherein said media contained in said enclosure of said reflector means is air.

* * * * *